(12) United States Patent
Greter et al.

(10) Patent No.: US 9,352,353 B2
(45) Date of Patent: May 31, 2016

(54) CONNECTOR FOR A DISCHARGE DEVICE

(75) Inventors: Andy Greter, Baar (CH); Ralph Egon Kayser, Luzern (CH); Wilhelm A. Keller, Merlischachen (CH)

(73) Assignee: Kuros Biosurgery AG, Zurich (CH)

( * ) Notice: Subject to any disclaimer, the term of this patent is extended or adjusted under 35 U.S.C. 154(b) by 235 days.

(21) Appl. No.: 13/003,625

(22) PCT Filed: Jul. 21, 2009

(86) PCT No.: PCT/CH2009/000260
§ 371 (c)(1),
(2), (4) Date: Jan. 11, 2011

(87) PCT Pub. No.: WO2010/020061
PCT Pub. Date: Feb. 25, 2010

(65) Prior Publication Data
US 2011/0121035 A1      May 26, 2011

(51) Int. Cl.
| | | |
|---|---|---|
| B67D 7/06 | (2010.01) | |
| B05C 17/005 | (2006.01) | |
| A61C 9/00 | (2006.01) | |

(52) U.S. Cl.
CPC ......... *B05C 17/00506* (2013.01); *A61C 9/0026* (2013.01); *B05C 17/00553* (2013.01)

(58) Field of Classification Search
CPC ................... B05C 17/00506; B05C 17/00553; B05C 17/00516; A61C 9/0026
USPC ........ 222/145.5, 145.6, 145.1, 129, 325, 137, 222/567
See application file for complete search history.

(56) References Cited

U.S. PATENT DOCUMENTS 5,462,204 A * 10/1995 Finn .............................. 222/137
6,527,203 B2 * 3/2003 Hurray et al. .................. 239/413
(Continued)

FOREIGN PATENT DOCUMENTS

| CN | 1852762 A | 10/2006 |
|---|---|---|
| CN | 101203327 A | 6/2008 |

(Continued)

OTHER PUBLICATIONS

English translation of foreign Office Action corresponding to Japanese Patent Application No. 2011-523285, dated Apr. 16, 2013. English language translation.

(Continued)

*Primary Examiner* — Patrick M Buechner
*Assistant Examiner* — Jeremy W Carroll
(74) *Attorney, Agent, or Firm* — Pabst Patent Group LLP

(57) ABSTRACT

The invention relates to a discharge device (1) comprising a tank housing (3) having at least one outlet (4) at one end and having a drive means at the opposite end. A connector (6) can be placed over the outlet (4) on the discharge device. The connector comprises a releasable mounting device that can be released by manual pressure on two opposite side surfaces of the connector. One guide surface (9) is provided on each of the two opposite side surfaces, each being oriented diagonally to the longitudinal axis (L) of the discharge device (1) and spaced in the direction of the discharge device. The connector is placed over the outlet on the discharge device in a mounting position. The guide surfaces (9) are moved radially toward each other in a released position by pressure (F) on the side surfaces. The guide surfaces thereby slide on an edge (15) of the discharge device (1), and the force is diverted to the edge (15), so that the connector (6) is axially displaced away from the drive direction in the released position.

14 Claims, 5 Drawing Sheets

(56) References Cited

U.S. PATENT DOCUMENTS

| | | | |
|---|---|---|---|
| RE38,399 E | | 1/2004 | Montgomery |
| 6,840,462 B2* | | 1/2005 | Hurray et al. ............... 239/413 |
| 7,316,330 B2 | | 1/2008 | Muller et al. |
| 2004/0222181 A1 | | 11/2004 | Biesecker et al. |
| 2005/0230422 A1* | | 10/2005 | Muller et al. ............ 222/145.6 |
| 2006/0227653 A1 | | 10/2006 | Keller |
| 2008/0056065 A1* | | 3/2008 | Keller ......................... 366/339 |
| 2008/0083782 A1* | | 4/2008 | Heusser et al. ............ 222/145.5 |
| 2009/0127289 A1 | | 5/2009 | Keller |
| 2009/0230214 A1* | | 9/2009 | Keller ......................... 239/338 |
| 2011/0108573 A1* | | 5/2011 | Stoeckli et al. ............... 222/87 |

FOREIGN PATENT DOCUMENTS

| | | |
|---|---|---|
| DE | 20 2006 004 738 U1 | 6/2006 |
| JP | 60136941 U | 9/1985 |
| JP | 6140355 U | 3/1986 |
| WO | 2007/109915 A1 | 10/2007 |
| WO | 2007/131371 A1 | 11/2007 |

OTHER PUBLICATIONS

Chinese Office Action issued Dec. 6, 2012 in a corresponding Chinese Patent Application No. 200980132404.3.

\* cited by examiner

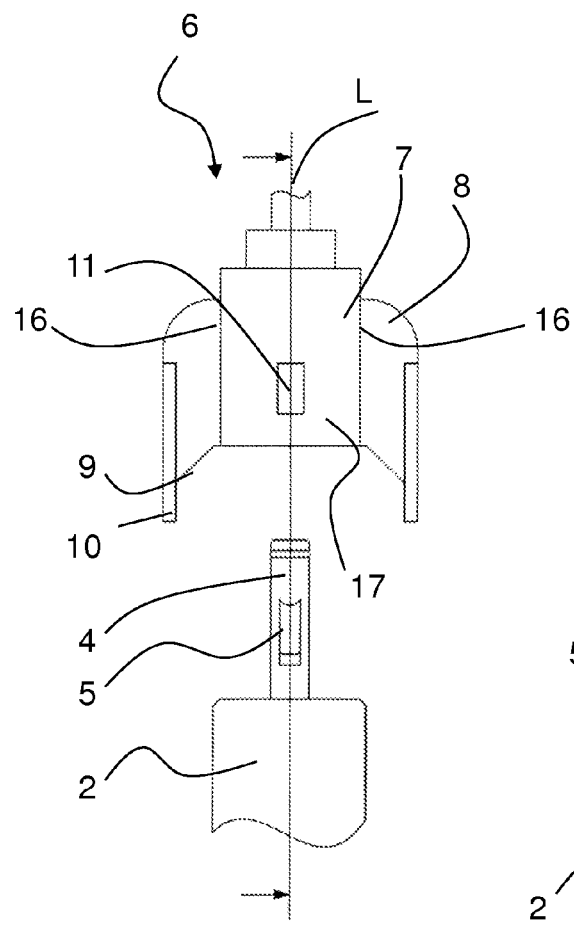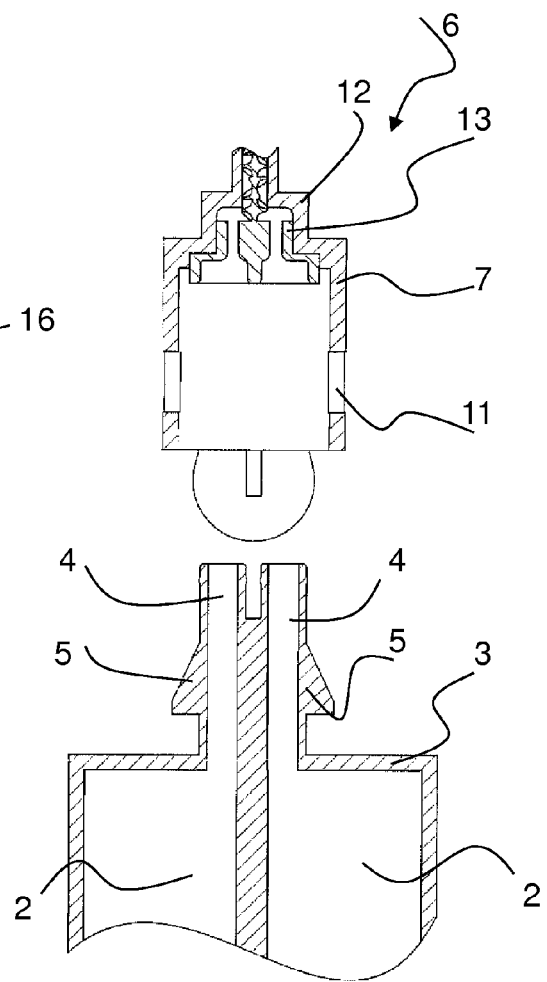
FIG. 2a
FIG. 2b

CONNECTOR FOR A DISCHARGE DEVICE

The present invention relates to a connector for connection to a discharge device, and a discharge device having such a connector, in particular a discharge device with at least two containers for the mixing of components.

PRIOR ART

The prior art discloses numerous syringes, double syringes, cartridges or double cartridges with at least one outlet, to which accessories are connected on the outlet or outlets for the purpose of discharging the components. Such accessories are, for example, mixers, discharge tips, spray nozzles, sheet-type nozzles, venting devices or adaptors for further elements of the discharge device. Accessories are usually attached over the outlets of the discharge device by means of a Luer Lock connection, a screw fastening or a snap fastening. A bayonet fastening may also be envisaged.

WO 2007/109915 discloses, for example, a discharge device with a removable accessory in the form of a mixer. The mixer is put in place on the outlets of the discharge device by means of a snap connection. The snap connection comprises snap noses on the outlet and snap orifices on a housing sleeve of the mixer. In the put-in-place state the snap noses snap into the snap orifices and hold the mixer on the discharge device. The snap orifices are in this case provided opposite one another on the mixer sleeve. To release the snap connection, the mixer sleeve is pressed together on the two mutually opposite sides of the sleeve which are arranged so as to be offset at 90° to the orifices. In this case, the mixer sleeve expands radially in the regions having the snap orifices, so that the snap noses are freed from the snap orifices. The mixer can then be pulled off from the discharge device in the axial direction.

DE 20 2006 004 738 U1 discloses a device for mixing two fluids, in which a mixing attachment can be put in place over the outlets of two syringes. The mixing attachment is held on the outlets by a snap connection. For this purpose, snap bars are provided on two mutually opposite sides and are arranged in the manner of a rocker on the side of the mixer attachment. The snap bars are arranged flexibly in such a way that, in an initial state, they engage behind the snap projection on the syringes and hold the mixing attachment on the syringes. For release, the bars can be pressed together at the ends which lie opposite the snap hooks, so that the snap hooks are released from the snap projections by virtue of the rocking function. As soon as the snap hooks are released, the mixing attachment can be pulled off from the syringes axially. A similar system is shown in U.S. Pat. No. 7,316,330 B2, in which flexible snap hooks on an accessory attachment can be released from a snap connection by being pressed together laterally, and the accessory attachment can thus be pulled off from the system axially.

With the accessory elements and connectors for discharge devices according to the prior art, the release of the accessory takes place in two steps. First, by the accessory being pressed together laterally, the holding arrangement has to be released, which holds the accessory on the discharge device. Axial force then has to be applied so that the accessory can be removed from the discharge device. The force applied axially must in this case overcome the adhesive force, frictional force and possibly slight jamming between the accessories and the discharge device. The result of this is that the connection between the accessory and the discharge device is released abruptly. Such an abrupt pull-off of the accessory may entail a risk of injury for the user. For example, such an uncontrolled abrupt movement may result in a stab wound on a cannula or needle of an accessory. The jolt when the accessory is being pulled off may also lead to small quantities of the components forming aerosols outside the discharge device, and this may give rise, for example, to an undesirable contamination of the working environment.

An object of the present invention, therefore, is to provide a connector for connection to a discharge device, which can be removed from the discharge device simply and safely, in which removal from the discharge device does not have an adverse effect on the components in the discharge device, and in which only a few work steps or manipulations are required for removal.

Furthermore, an object of the present invention is to provide a discharge device having at least two containers, in which a connector can be put in place and removed in a simple way, without the risk of injury or adverse effects upon the components in the containers.

SUMMARY OF THE INVENTION

This object is achieved by means of a connector as claimed in claim 1 and a discharge device as claimed in claim 10. Advantageous embodiments of the connector and of the discharge device are described in the dependent claims.

According to the present invention, a discharge device is provided which comprises a container housing with at least one outlet at one end and with a drive means at the opposite end. The container housing preferably comprises at least two containers which are accommodated in the housing or together form a container housing. The containers or the container housing are preferably designed as multicomponent cartridges or multicomponent syringes, in particular as double syringes. The containers have in each case outlets which, arranged next to one another on the container housing, are provided at one end. At the opposite end, the drive means for discharging the components through the outlets of the containers is provided. A simple manually actuated drive rod may serve, for example, as drive means. A connector according to the invention for connection to the discharge device is attached releasably over the outlet or outlets by means of a holding arrangement. The holding arrangement is releasable by means of manual pressure on two opposite side faces of the connector.

A releasable fastening may serve, for example, as a holding arrangement and is effected simply by the connector being pushed axially onto the outlets or the container housing without a rotational movement, for example by means of a form fit. However, a holding arrangement with rotational movement, such as, for example, a bayonet connection, may also basically be envisaged. Furthermore, the holding arrangement may also be effected simply by the connector being pushed nonpositively onto the outlets, the connector being held as a result of the frictional connection between the structural parts. The holding arrangement is preferably formed by a latching connection in which two latching elements latch releasably with one another.

According to the present invention, a guide face is provided on each of the two opposite side faces of the connector which are provided for releasing the holding arrangement as a result of the application of manual pressure to the side faces. The two guide faces arranged opposite one another are oriented in such a way that they in each case project obliquely with respect to the longitudinal direction of the discharge device in the direction of the latter. The guide faces may have a width which corresponds approximately to the diameter of a container of the discharge device. The guide faces may have a width which corresponds approximately to the diameter of a container of the discharge device. Preferably, the guide faces are designed as guide edges of small width. Thus, according to the invention, the guide faces or edges project in an arrow-like manner from the connector. Preferably, the faces or edges form an angle of between 30° and 90°, especially preferably of 45°.

In a holding position, the connector is attached to the discharge device over the outlet or outlets or is held in the holding position by the holding arrangement. Preferably, the connector is provided completely over the outlets in the holding position. In a release position, the guide faces are moved radially toward one another by means of pressure upon the side face. In this case, the guide faces slide on an edge of the discharge device, in particular of the container housing or containers, the laterally acting pressure force being deflected onto the edge of the discharge device and therefore acting in the axial direction. As a result of the sliding of the guide faces, the connector is displaced axially away from the discharge device in the release position. The axial displacement of the connector in relation to the container housing, or to the containers, takes place by the oblique guide faces being pressed onto the edges, so that a force vector in the axial direction is generated as a result of the oblique impingement of the guide faces upon the edges.

The connector can thereby be removed from the discharge device in a controlled and guided manner. An abrupt pull-off in the axial direction of the discharge device is not necessary or is necessary to only a very slight degree. Consequently, the removal of the connector from the discharge device can be simplified markedly for the user, and the risk of injury arising in this case can be reduced. Furthermore, there is no risk of a formation of aerosols, as is the case during an abrupt pull-off.

The connector preferably comprises a sleeve or a jacket which can be slipped over the outlets so as to put the connector in place over these. The connector sleeve has flanks which project from the outer circumference on two opposite sides and on which the guide faces are provided. The flanks may be attached in a plate-like manner in the longitudinal direction along the sleeve. It is in this case essential that the guide faces on the flanks lie opposite an edge on the discharge device or on the container housing or containers. Preferably, the flanks are arranged on the connector sleeves so as to project laterally in such a way that at least the guide faces project beyond a margin of the connector sleeve. The flanks thus have the guide faces on their sides directed inward with respect to the longitudinal axis. The guide faces therefore in each case project obliquely with respect to the longitudinal direction of the discharge device beyond the margin of the connector sleeve.

The connector sleeve does not have to be designed in the manner of a ring. The sleeve may also have an oval or elliptic cross section. In this case, preferably, the guide faces are provided on the remotely located opposite sides, and the holding arrangement is provided on the two nearer opposite sides. Depending on the design or arrangement of the outlets, the connector sleeve may be designed in a suitable form so that the outlets can be received in it. Preferably, however, the connector sleeve is designed as a round sleeve. The sleeve may also taper conically in the discharge direction. Preferably, however, the connector sleeve is provided cylindrically.

Pressure faces, for example in the form of small pressure plates, for grasping the connector when the holding arrangement is being released may be provided on the flanks of the connector sleeve. Since the flanks run perpendicularly with respect to the circumference of the connector sleeve, the pressure faces are slightly lifted off from the circumference of the sleeve and run essentially parallel to the circumferential face. This arrangement increases the spacing between the lateral pressure points on the connector, thus making it easier to grasp and press together the side faces of the connector.

In an advantageous embodiment of the connector, the pressure point for applying the pressure force upon the side faces of the connector lies, offset axially, outside the circumference of the connector sleeve. It can thereby be ensured that the pressure point is provided on the outermost margin of the connector sleeve or outside. Further, it is advantageous to provide the pressure faces provided on the flanks in such a way that they project beyond the margin of the connector sleeve and spread slightly in this direction. Spreading, in turn, increases the spacing between the engagement points when the connector sleeve is being pressed together. This gives rise to a kind of lever effect which allows an efficient transmission of the laterally engaging pressure force to the guide faces on the connector sleeve and therefore to the edge of the discharge device.

In an advantageous embodiment of a connector according to the present invention, the holding arrangement is provided on opposite sides of the connector sleeve between the connector sleeve and the outlet or outlets. The two opposite sides are provided so as to be offset at 90° with respect to the side faces having the guide faces according to the present invention. The guide faces and the holding arrangement are therefore arranged crosswise.

The holding arrangement may be provided by a releasable latching connection which has at least one latching projection and at least one latching depression, of which one is arranged on the connector and the other on an outlet in such a way that a latching projection comes to lie opposite a latching depression. In the holding position, a latching projection engages into a latching depression, and movement of the connector in the axial direction away from the discharge device is blocked. In the release position, the two opposite sides of the connector sleeve which have the latching arrangement are widened radially and the latching projection is released from the latching depression or the latching projections are released from the latching depressions. Widening takes place by the two opposite side faces of the connector sleeve being pressed together manually. By these two side faces being pressed together, the two sides, offset at 90°, of the connector sleeve, which carry the latching connection, are widened.

Simultaneously with the release of the latching connection, the oblique guide face also slides on the edge of the discharge device or of the container housing and lifts the connector away from the discharge device in the axial direction. Thus, in the release of a connector according to the present invention, only a single manipulation, to be precise pressing the side faces together, is necessary in order both to release the holding arrangement and to remove the connector from the discharge device.

A device for orienting the connector with respect to the discharge device may be provided on the outside of the connector. This purpose may be served, for example, by a web or a groove or also merely a line on the connector. Preferably, the device is designed in such a way that the connector can be attached only in the oriented position to the discharge device in the holding position. This may take place, for example, by means of the configuration of the holding arrangement, the elements of which engage one in the other in one specific position only.

An advantage of the present invention is that both the release of the holding arrangement and the pull-off of the connector from the discharge device are provided by arrangements on a single structural part, to be precise the connector sleeve with the guide faces and the holding arrangement. The connector sleeve thus serves both as part of the holding arrangement for holding the connector and the discharge device and for detaching the connector from the discharge device.

According to a further aspect, the invention comprises a discharge device with a connector, as is described above. Preferably, in a holding position, the connector surrounds the outlets in a liquid-tight manner. For this purpose, a tight fit of the connector over the outlets is provided, which is achieved by means of an insert element inside the connector sleeve, said insert element coming to lie within the exact fit on the outer circumference of the outlets. To release the tight fit in the release position of the connector from the discharge device, once again, the lateral faces of the connector having the guide faces are pressed together, so that, by the guide faces being guided on the edge of the discharge device or of the container housing, the holding force is overcome in a controlled way and the tight fit is released.

In one embodiment of the present invention, the pressure faces of the flanks of the connector project in the axial direction beyond the container housing or the pressure faces at least partially overlap the container housing. As a result, the area of the pressure faces can be increased, and it becomes easier to exert force upon the side faces of the connector. Preferably, the connector is arranged, in the holding position, over the outlets of the containers in such a way that the individual outlets are converged in a canal provided in the connector. Mixing of the individual components from the containers of the discharge device can then take place in the canal.

In another embodiment, the connector may have at least one access canal, preferably in each case an access canal for each outlet, which, in the holding position of the connector and the discharge device, makes a fluid connection with the respective outlet. A connector designed in this way may serve for filling the containers of the discharge device.

In a discharge device with a connector according to the present invention, there is no need for any effort in the axial direction in order to pull off the connector. As described above, it is sufficient to press the two side faces of the connector together. As a result of the two oblique guide faces, a jolt-free and controlled removal of the connector from the discharge device consequently becomes possible. Owing to the two pressure faces which are arranged laterally on the side faces, an ergonomic shape of the connector is achieved which makes it simpler to press the side faces together laterally. Even in the event of gumming-up or contamination between the connector and the discharge device, simple removal of the connector from the discharge device can be carried out by means of the oblique guide faces according to the invention.

BRIEF DESCRIPTION OF THE DRAWINGS

Preferred embodiments of the invention are illustrated with reference to the drawing which is in no way to be interpreted restrictively. Features of the invention which are disclosed by the figures of the drawing are to be understood as belonging to the disclosure. In the drawing:

FIG. 2a shows a schematic lateral illustration of a connector and a part of a discharge device from a first side;

FIG. 2b shows a sectional illustration, rotated through 90° with respect to the illustration according to FIG. 2a;

FIG. 3b shows a sectional illustration rotated through 90° with respect to FIG. 3a;

FIG. 4b shows a sectional illustration rotated through 90° with respect to FIG. 4a;

FIG. 1 shows a discharge device 1 with two containers 2, the two containers being combined into a container housing 3. Two outlets 4 are provided at one end of the container housing and are arranged in a tube-like manner next to and parallel to one another. The outlets have in each case a latching projection 5 on their sides facing away from one another. The discharge device is suitable, for example, for the mixing of two components which are accommodated in each case in one of the containers 2. The discharge device may be provided, at the end which lies opposite the outlets 2, with a drive means which, for example, by being pushed into the containers, discharges the component through the outlets. The discharge device may in this sense be designed, for example, as a double syringe.

Figure 1:
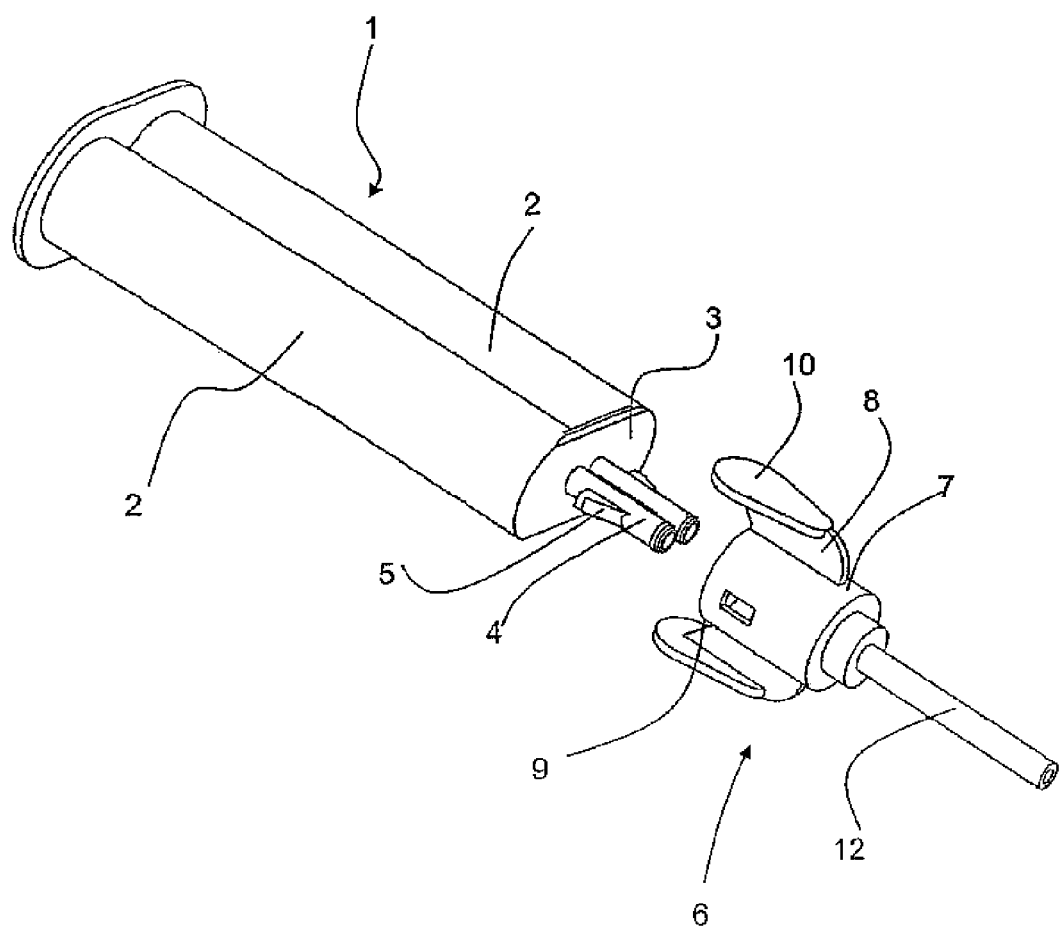
FIG. 1 illustrates an exploded illustration of a discharge device with connector.

A connector 6 can be put in place as an accessory onto the discharge device 1. In the present exemplary embodiment, the accessory is formed by an attachable discharge nozzle. The connector has a connector sleeve 7 which has a circular cross section. A flank 8 is provided on each of two opposite sides of the sleeve 7, which flank 8 projects perpendicularly from the surface of the sleeve 7 and at its end facing the discharge device projects beyond the margin of the sleeve 7. Arranged in each case on the projecting part of the flank 8 is a guide face 9 which in each case runs obliquely with respect to the longitudinal axis of the discharge device and is oriented so as to project in the direction of the latter.

The guide faces preferably form the same angle to the longitudinal axis. The angle preferably amounts to approximately 45°. On the outer edge of the flank 8, pressure faces 10 are arranged which run in the circumferential direction nearly parallel to the circumference of the sleeve 7 and are arranged so as to be raised slightly in the direction of the discharge device in the longitudinal direction. The pressure faces are provided on the flank 8 in such a way that their faces project beyond the guide faces 9 in the direction of the discharge device.

Latching orifices 11 are provided in a circumference on the two opposite faces of the connector sleeve 7 which are offset at approximately 90° with respect to the pressure faces 10. In the example illustrated, the latching orifices 11 extend completely through the circumferential wall of the sleeve 7. It is also conceivable, however, that only latching depressions in the inner circumferential face of the sleeve 7 are provided instead of the orifices. The latching orifices 11 cooperate with the latching projections 5 when the connector 6 is being put in place on the discharge device 1.

The connector 6 has a discharge nozzle 12 at the end which faces away from the discharge device 1. When the connector is put in place on the discharge device, the content of the container 2 can be discharged through the outlets 4 and the discharge nozzle 12 by the drive means.

FIG. 2a shows a schematic illustration of the connector and a part of the discharge device with the outlets from a first side. FIG. 2b shows the same elements as a sectional illustration in a view rotated through 90° with respect to FIG. 2a. The connector 6 with the sleeve 7 and a latching orifice 11 and with the flanks 8 located on opposite sides 16, 17 and having the guide faces 9 and the pressure faces 10 can be seen in FIG. 2a. The longitudinal axis L runs along the axis of the sleeve 7. The guide faces 9 project in an arrow-like manner from the sleeve 7. The discharge device is shown in FIG. 2a from the side in such a way that the two outlets 4 come to lie one behind the other. A latching projection 5 is shown on the front side of the illustration and on the side of an outlet 4. The outlet 4 is connected to the container 2.

In FIG. 2b, a section through the container housing 3 is evident, the latter receiving in it the two containers 2 to which the outlets 4 are connected. The latching projections 5 can be seen in each case diametrically on that side of an outlet 4 which faces away from the adjacent outlet. The connector 6 is shown from the side, as it is being put in place on the discharge device 1.

The latching orifices 11 are evident in the connector sleeve 7. Inside the sleeve 7, an insert element 13 is arranged which can surround the ends of the outlets 4 so that a liquid-tight connection is preferably obtained. The insert element 13 has for each outlet a canal which leads to the discharge nozzle 12.

Figure 3A:
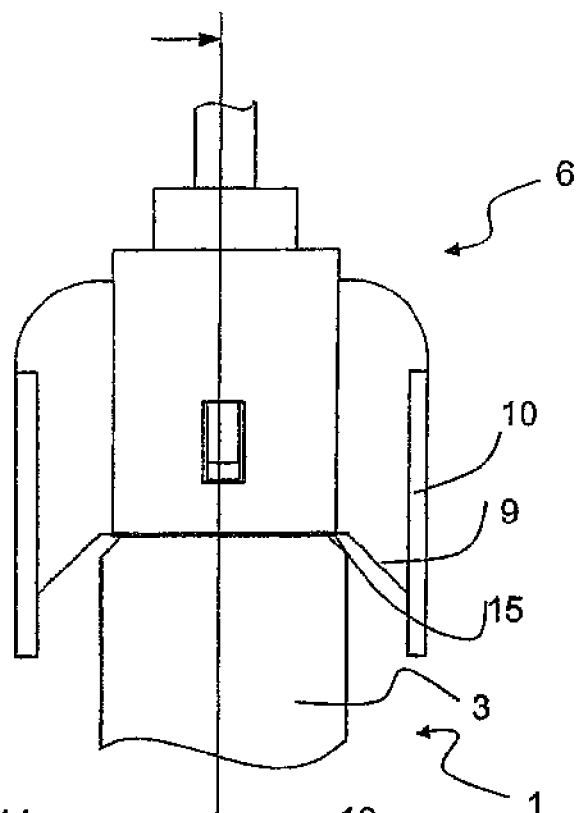
FIG. 3a shows a lateral illustration of a discharge device with a connector in a holding position.
Figure 3B:
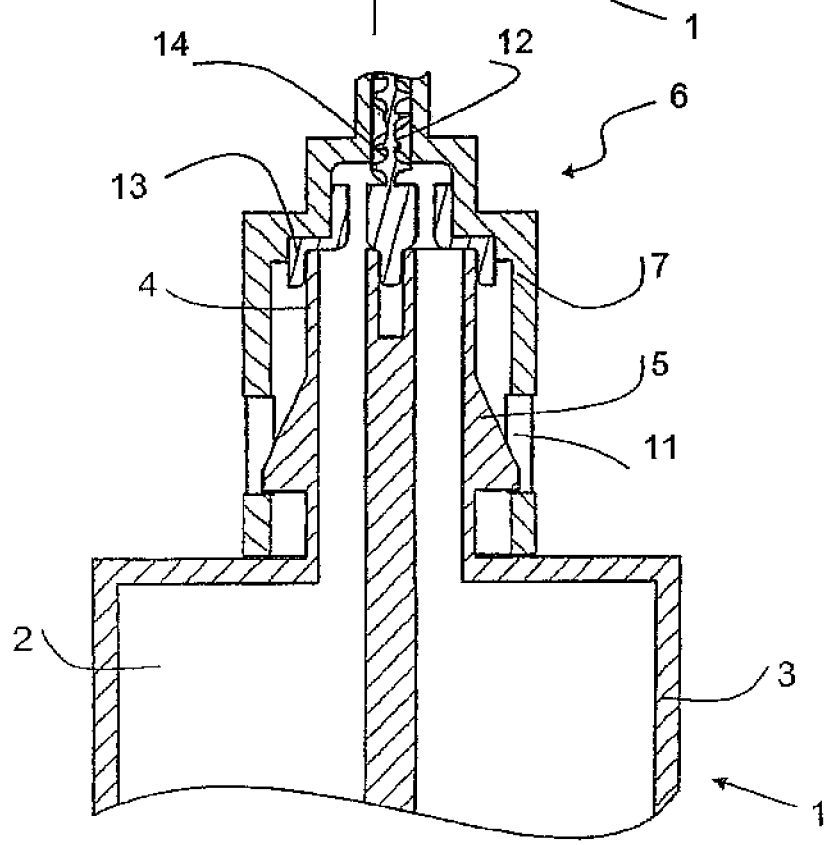

In FIGS. 3a and 3b, the connector 6 is put in place in a holding position on the discharge device 1. As is evident in FIG. 3b, in the holding position the latching projections 5 project into the latching orifices 11 of the sleeve 7, so that the edges of the latching projections and of the latching orifices lie opposite one another in such a way that they block movement of the connector 6 in the axial direction away from the discharge device 1. In FIG. 3b, it is clear how the end of the outlet 4 is surrounded by the insert element 13. This gives rise to a continuous fluid connection out of the inside of the containers 2 as far as the discharge nozzle 12. Inside the discharge nozzle 12 is arranged a mixing device 14 which serves for mixing the components discharged from the two containers 2. As is evident in FIG. 3a, the oblique guide faces 9 come to lie opposite the edges 15 of the container housing 3. No force is exerted upon the pressure faces 10, so that the connector 6 is held on the discharge device 1 by the holding arrangement in the form of the latching connection.

Figure 4A:
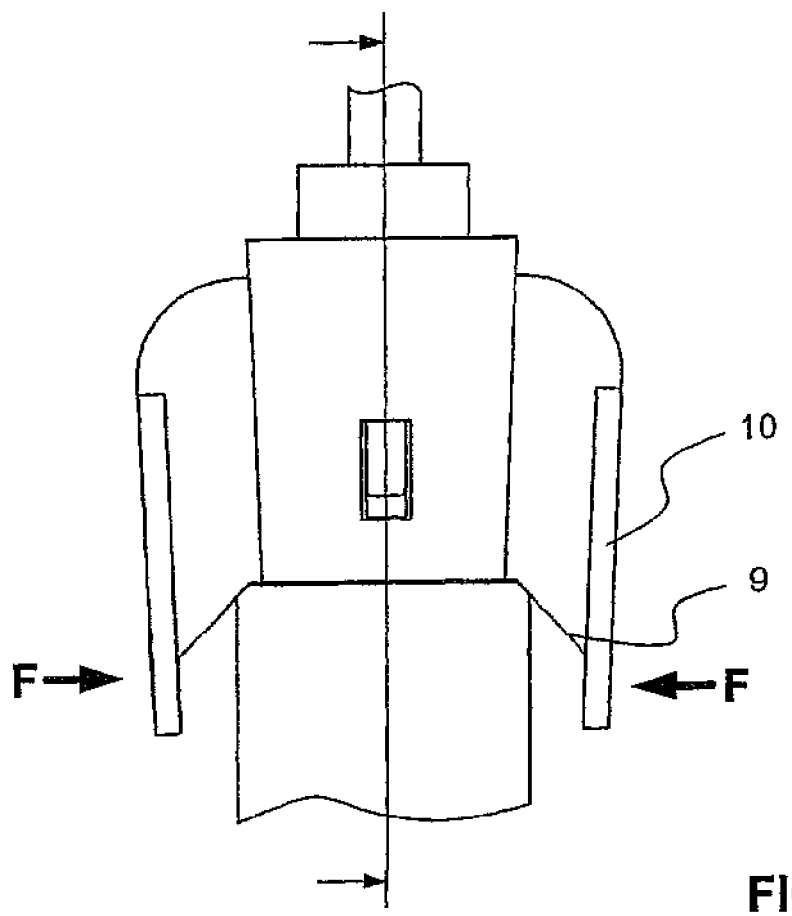
FIG. 4a shows a lateral illustration of a discharge device with a connector under the action of lateral force.
Figure 4B:
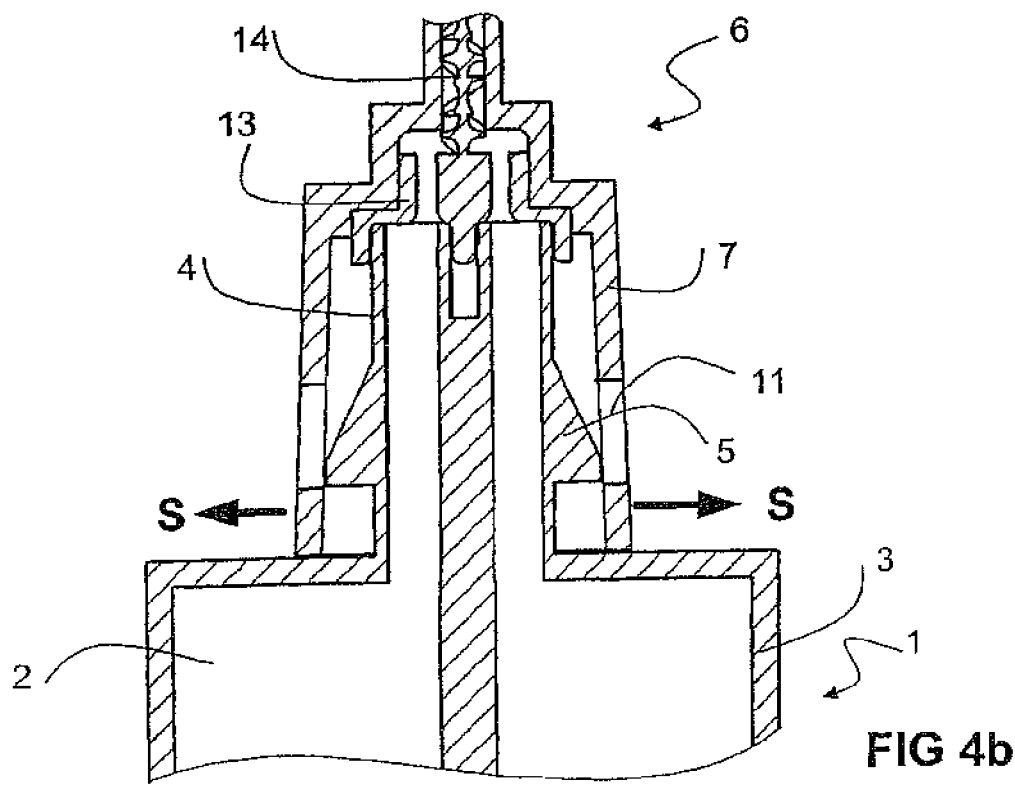

FIGS. 4a and 4b show the connector 6 under the action of lateral force upon the pressure faces 10. For this purpose, the connector 6 is grasped with two fingers, one on each side, and is pressed together, with the result that a force in the direction of the arrow F is exerted on the side faces of the connector in a radial direction with respect to the longitudinal axis. In this case, the guide faces 9 come to lie on the edges 15.

It is shown in FIG. 4b how the two lateral faces of the sleeve 7 which are rotated through 90° with respect to the pressure faces 10 spread in the direction of the arrows S as soon as a radially acting force F is exerted upon the pressure faces 10. In this case, these sides of the sleeve 7 widen radially outward, so that the latching orifices 11 come to lie outside the edges of the latching projections 5. In this position, there is no blocking of the connector 6 in the direction of axial movement away from the discharge device 1.

Figure 5A:
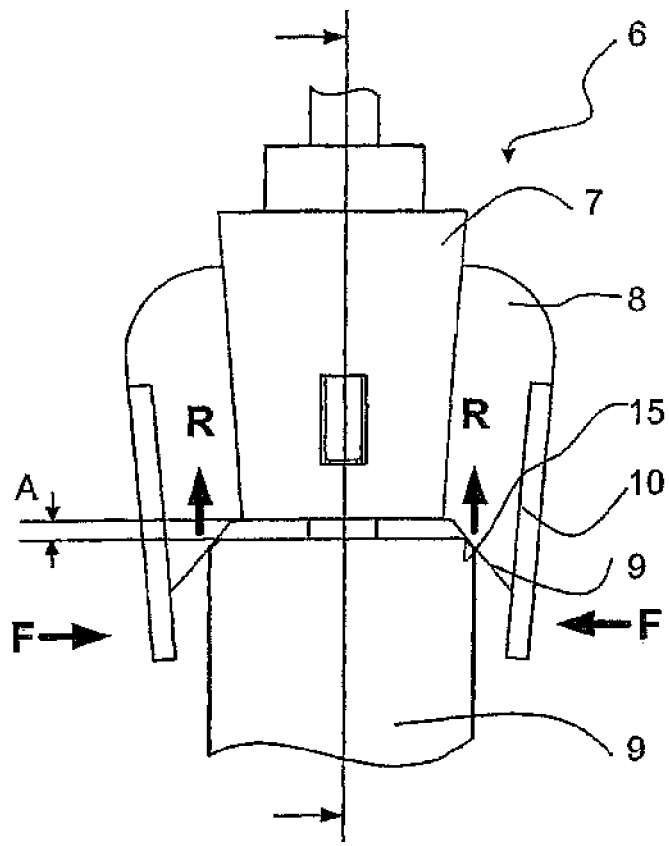
FIG. 5a illustrates a lateral illustration of a discharge device with a connector in a release position.
Figure 5B:
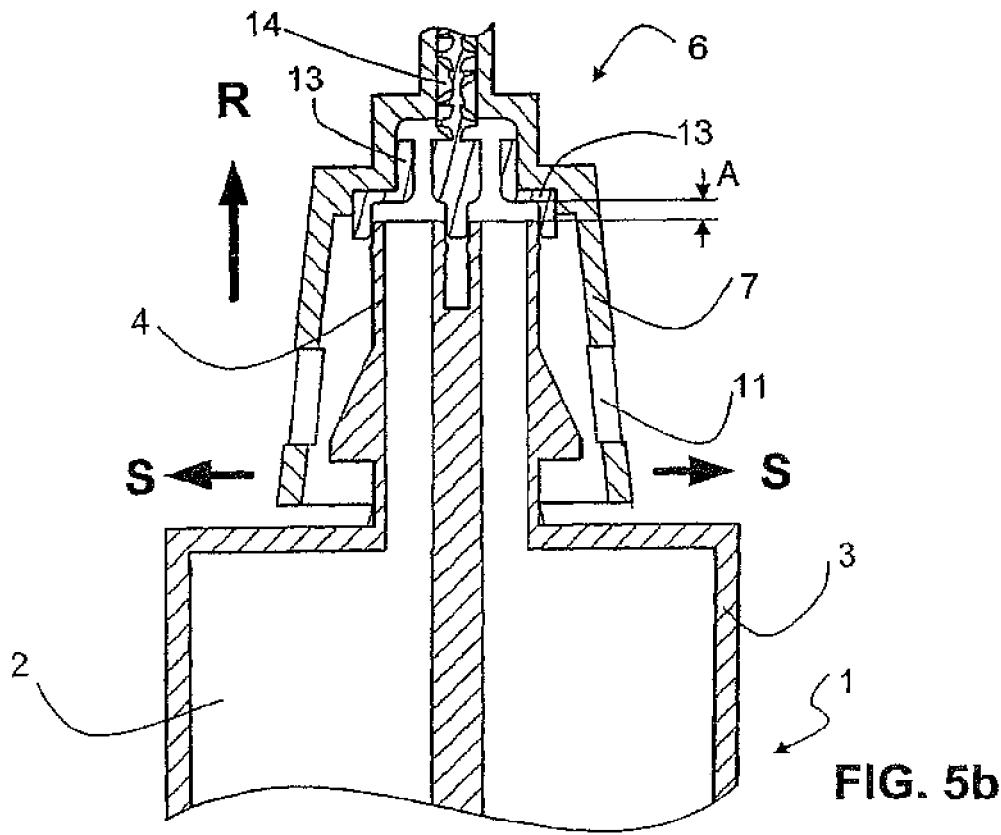
FIG. 5b shows a sectional illustration according to FIG. 5a, rotated through 90°.

FIGS. 5a and 5b show the connector 6 in a release position. In this case, a pressure force has continued to be exerted in the direction of the arrows F upon the pressure faces 10 on the connector sleeve 7. As is evident in FIG. 5a, in this case the oblique guide faces 9 are guided along the edges 15 on the container housing 3. The force F applied in the radial direction perpendicularly to the pressure faces 10 is in this case deflected into a component in the axial direction according to the arrow R. The guide faces 9 in this case slip on the edge 15 and, as a result of the force component R, lift off the connector 6 from the container housing 3 in a controlled way. In FIG. 5a, the connector 6 is lifted off from the container housing 3 by the amount of the distance A.

It is shown in FIG. 5b how the sides of the connector sleeve 7 which are located between the guide faces 9 with the latching orifices 11 are widened in the direction of the arrows S. By the guide faces 9 sliding on the edges 15 and by the connector 6 consequently being lifted from the container housing 3, the insert element 13 is also lifted off in the axial direction from the end of the outlets 4 by the amount of the distance A. The tight fit between the insert element 13 and the outlets 4 is thus cancelled. The latching connection between the latching orifices 11 and the latching projections 5 is likewise cancelled, as is already illustrated in FIG. 4b. In the release position shown, the connector 6 can be removed from the container housing 3 without further effort. There is no abrupt separation of the connector 6 from the container housing 3 of the discharge device 1, since any holding arrangements or holding connections have already been released, in that the connector 6 has been lifted off in the axial direction from the container housing 3 in a controlled way as a result of the sliding of the guide faces 9 on the edges 15.

LIST OF REFERENCE SYMBOLS

1 Discharge device
2 Container
3 Container housing
4 Outlet
5 Latching projection
6 Connector
7 Connector sleeve
8 Flank
9 Guide face
10 Pressure face
11 Latching orifice
12 Discharge nozzle
13 Insert element
14 Mixing device
15 Edge
L Longitudinal axis
F Force, radial
R Force, axial
A Distance
S Direction of widening

The invention claimed is:

1. A connector for connection to a discharge device, the discharge device comprising a container housing with at least one outlet at a first end and with a drive means at a second end that is opposite to the first end, the connector comprising:
 a connector sleeve having an outer circumference and defining a first pair of opposite sides and a second pair of opposite sides, the second pair of opposite sides being offset at 90° with respect to the first pair of opposite sides;
 a holding arrangement by which the connector is attachable releasably over the at least one outlet, the holding arrangement forming a releasable latching connection between the connector and the discharge device, the releasable latching connection being releasable by means of manual pressure on the first pair of opposite sides of the connector sleeve, the releasable latching connection including at least one latching projection and at least one latching depression which are arranged so as to be distributed opposite one another on the second pair of opposite sides of the connector sleeve and on the at least one outlet; and
 two flanks projecting laterally from the first pair of opposite sides of the connector sleeve, each flank defining a guide face that is oriented obliquely with respect to a longitudinal axis of the discharge device, each guide face being directed inwardly with respect to the longitudinal axis towards the first end of the discharge device, the connector being held on the discharge device over the outlet in a holding position, the latching projection engaging into the latching depression and blocking movement of the connector in an axial direction away from the discharge device, and in a release position, the second pair of opposite sides of the connector sleeve on which the latching connection is formed being widened radially, the latching projection being released from the latching depression, and the guide faces being arranged in such a manner that the guide faces move radially toward one another when an inwardly directed pressure force is applied on the guide faces, said movement causing the guide faces to slide on an edge of the discharge device so that the inwardly directed pressure force in the absence of an applied force in the axial direction is deflected by the edge to cause an axial force on the connector, the axial force acting to displace the connector axially away from the discharge device, so as to axially lift off the connector from the discharge device.

2. The connector as claimed in claim 1, wherein the flanks project axially beyond a margin of the connector sleeve.

3. The connector as claimed in claim 1, further comprising pressure faces for grasping the connector, the pressure faces being arranged on the flanks.

4. The connector as claimed in claim 3, wherein the pressure faces are formed by pressure plates, the pressure plates being arranged essentially perpendicular to the flanks.

5. The connector as claimed in claim 1, wherein a pressure point for applying the pressure force (F) to the first pair of opposite sides lies, offset axially, outside the circumference of the connector sleeve.

6. The connector as claimed in claim 1, wherein the connector sleeve, the flanks with the guide faces, and the holding arrangement are made in one piece.

7. The connector of claim 1, wherein the at least one latching depression is located in the second pair of opposite sides.

8. A discharge device comprising:
at least two containers, each with a first and a second end and an outlet, the containers being accommodated in a container housing or forming a container housing, and a component being accommodated in each of the containers, the outlets being arranged next to one another at the first end of the container housing; and a connector comprising:
a connector sleeve having an outer circumference and defining a first pair of opposite sides and a second pair of opposite sides, the second pair of opposite sides being offset at 90° with respect to the first pair of opposite sides;

a holding arrangement by which the connector is attachable releasably over the outlets, the holding arrangement forming a releasable latching connection between the connector and the container housing, the releasable latching connection being releasable by means of manual pressure on the first pair of opposite sides of the connector, the releasable latching connection including at least one latching projection and at least one latching depression which are arranged so as to be distributed opposite one another on the second pair of opposite sides of the connector sleeve and on the outlets; and two flanks projecting laterally from the first pair of opposite sides of the connector sleeve, each flank defining a guide face that is oriented obliquely with respect to a longitudinal axis of the discharge device, each guide face being directed inwardly with respect to the longitudinal axis, in the direction of the first end of the container housing, the connector being held on the container housing over the outlet in a holding position, the latching projection engaging into the latching depression and blocking movement of the connector in an axial direction away from the container housing, and in a release position, the second pair of opposite sides of the connector sleeve on which the latching connection is formed being widened radially, the latching projection being released from the latching depression, and the guide faces being arranged in such a manner that the guide faces move radially toward one another when an inwardly directed pressure force is applied on the guide faces, said movement causing the guide faces to slide on an edge of the container housing so that the inwardly directed pressure force in the absence of an applied force in the axial direction is deflected by the edge to cause an axial force on the connector, the axial force acting to displace the connector axially away from the container housing after the releasable latching connection has been released, so as to axially lift off the connector from the container housing.

9. The discharge device as claimed in claim 8, wherein, in the holding position, the connector surrounds the outlets in a liquid-tight manner with a tight fit and, in the release position, the holding fit is released.

10. The discharge device as claimed in claim 8, wherein the connector further comprises pressure faces for grasping the connector, the pressure faces being arranged on the flanks, the pressure faces projecting in the axial direction beyond the container housing.

11. The discharge device as claimed in claim 10, wherein the pressure faces are formed by pressure plates, the pressure plates being arranged essentially perpendicular to the flanks.

12. The connector as claimed in claim 8, wherein, in the holding position, the connector converges the outlets of the containers into a canal provided in the connector.

13. The discharge device as claimed in claim 8, wherein the connector has for each outlet at least one access canal which, in the holding position, makes a fluid connection with the outlet.

14. The discharge device of claim 8, wherein the at least one latching depression is located in the second pair of opposite sides.

* * * * *